US005246612A

United States Patent [19]

[11] Patent Number: 5,246,612

[45] **Date of Patent: * Sep. 21, 1993**

Van Dijk et al.

[54] MACHINE DISHWASHING COMPOSITION CONTAINING PEROXYGEN BLEACH, MANGANESE COMPLEX AND ENZYMES

[75] Inventors: Willem R. Van Dijk, Oud Beyerland; Ton Swarthoff, Hellevoetsluis, both of Netherlands

[73] Assignee: Lever Brothers Company, Division of Conopco, Inc., New York, N.Y.

[ * ] Notice: The portion of the term of this patent subsequent to Mar. 16, 2010 has been disclaimed.

[21] Appl. No.: 934,149

[22] Filed: Aug. 21, 1992

[30] Foreign Application Priority Data

Aug. 23, 1991 [GB] United Kingdom ................. 9118242

[51] Int. Cl.[5] ..................... C11D 3/386; C11D 3/395; C12N 9/28; D06L 3/02

[52] U.S. Cl. ........................................ 252/102; 8/111; 252/99; 252/103; 252/174.12; 252/174.19; 252/174.24; 252/174.25; 252/186.38; 252/186.39; 252/524; 252/542; 252/DIG. 12

[58] Field of Search ............ 252/99, 102, 103, 186.38, 252/186.39, 174.12, 524, 542, DIG. 12; 8/111

[56] References Cited

U.S. PATENT DOCUMENTS

| | | | |
|---|---|---|---|
| 4,539,132 | 9/1985 | Oakes | 252/95 |
| 4,597,886 | 7/1986 | Goedhart | 252/95 |
| 4,626,373 | 12/1986 | Finch et al. | 252/96 |
| 4,631,141 | 12/1986 | Baxter | 252/95 |
| 4,728,455 | 3/1988 | Rerek | 252/99 |
| 4,810,410 | 3/1989 | Diakun | 252/102 |
| 4,889,651 | 12/1989 | Broze | 252/95 |
| 5,021,187 | 6/1991 | Harriott et al. | 252/186.38 |
| 5,114,606 | 5/1992 | Van Vliet et al. | 252/103 |
| 5,114,611 | 5/1992 | Van Kralingen et al. | 252/186.33 |
| 5,153,161 | 10/1992 | Kerschner et al. | 502/167 |
| 5,194,416 | 3/1993 | Jureller et al. | 502/167 |

FOREIGN PATENT DOCUMENTS

| | | |
|---|---|---|
| 42939/89 | 5/1990 | Australia . |
| 0306089 | 3/1989 | European Pat. Off. . |
| 0369841 | 5/1990 | European Pat. Off. . |
| 0458397 | 11/1991 | European Pat. Off. . |
| 0458398 | 11/1991 | European Pat. Off. . |

OTHER PUBLICATIONS

J. Am. Chem. Soc., (Weighardt et al.), 1988, vol. 110, pp. 7398-7411.

J. Chem. Soc. Chem. Comm., (Weighardt et al.), 1988, pp. 1145-1146.

*Primary Examiner*—Dennis Albrecht

*Attorney, Agent, or Firm*—A. Kate Huffman

[57] ABSTRACT

A machine dishwashing composition containing a peroxygen compund as the bleaching agent and having improved bleaching action combined with excellent starch removing properties is disclosed. The compositioncontains a dinuclear manganese complex having the general formula.

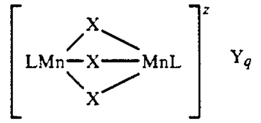

as defined in the description, as bleach catalyst and starch removing additive, in an amount corresponding to a Mn-content of from 0.0001 to about 1.0% by weight.

A preferred Mn-complex is: $[(Mn\text{-}TACN)Mn^{IV}(\mu\text{-}O)_3Mn^{IV}(Me\text{-}TACN)]^{2+}(PF_6^-)_2$ Best results are obtained when amylolytic is present in the composition.

11 Claims, 2 Drawing Sheets

MACHINE DISHWASHING COMPOSITION CONTAINING PEROXYGEN BLEACH, MANGANESE COMPLEX AND ENZYMES

FIELD OF THE INVENTION

This invention relates to detergent cleaning compositions especially adapted for use in automatic dishwashing machines.

BACKGROUND AND PRIOR ART

Conventional automatic machine dishwashing compositions are normally phosphate-based, highly alkaline products comprising a chlorine bleaching agent having a solution pH generally above 12.0. Though performance-wise these conventional products are quite satisfactory, they have some serious drawbacks in other aspects. First of all, highly alkaline compositions have the disadvantage of being aggressive and hazardous. Incorporation of chlorine bleaches, though effective for stain removal, requires special processing and storage precautions to protect the composition components from decomposition upon direct contact with active chlorine.

The stability of chlorine bleach is also critical and raises additional processing and storage difficulties. A further disadvantage is the difficulty of dyeing and perfuming of such compositions owing to incompatibility of many dyes and perfumes with chlorine. Finally, phosphate and phosphorus-containing components have been under attack, because of the general belief that they can lead to environmental problems.

It has been suggested that these drawbacks be overcome by formulating a reduced phosphate or phosphate-free machine dishwashing composition of lower alkalinity and using a milder oxygen bleach instead. To compensate reduced performance, particularly with respect to starch and protein removal, enzymes are added, especially amylolytic and proteolytic enzymes, such as amylases and proteases. The oxygen bleach used therein is sodium perborate or sodium percarbonate in conjunction with an organic activator or bleach precursor, e.g. N, N, N', N'-tetraacetylethylene diamine (TAED), which upon dissolution will react to form an organic peroxyacid, e.g. peracetic acid, as the bleaching species.

However, the performance of such mildly alkaline enzymatic dishwashing compositions is still far from ideal. Oxygen bleaches are generally poorer bleaching agents compared with chlorine bleaches. The use of an activated perborate for achieving a reasonable bleach performance, especially on tea stains, appears to be at the expense of the starch removal, due to incompatibility of amylases with stronger bleaching agents. Use of perborate alone, i.e. without TAED, would improve the starch removal, but the bleach performance is poor. It is thus the incompatibility of enzymes, particularly of amylases, with the bleach, that forms a major problem in the formulation of a satisfactory machine dishwashing composition comprising an oxygen bleach and enzymes.

Consequently, it is an object of the present invention to provide a machine dishwashing composition containing a peroxygen compound as the bleaching agent that will combine improved bleaching action with excellent starch removal properties.

DESCRIPTION OF THE INVENTION

It has now surprisingly been discovered that starch residues can be excellently removed to a much better extent, even in the absence of amylolytic enzymes, if the composition contains a bleaching system comprising a combination of a peroxygen compound and a dinuclear manganese complex of the following general formula:

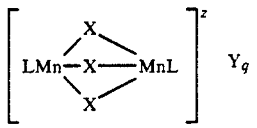

wherein Mn is manganese, which can individually be in the III or IV oxidation state; each x represents a coordinating or bridging species selected from the group consisting of $H_2O$, $O_2^{2-}$, $O^{2-}$, $OH^-$, $HO_2^-$, $SH^-$, $S^{2-}$, >SO, $Cl^-$, $N^{3-}$, $SCN^-$, $RCOO^-$, $NH_2^-$ and $NR_3$, with R being H, alkyl or aryl (optionally substituted); L is a ligand which is an organic molecule containing a number of nitrogen atoms which coordinates via all or some of its nitrogen atoms to the manganese centres; z denotes the charge of the complex and is an integer which can be positive or negative; Y is a monovalent or multivalent counter-ion, leading to charge neutrality, which is dependent upon the charge z of the complex; and $q = z/[\text{charge } Y]$.

Accordingly, in its broadest aspect the invention concerns the use of a dinuclear manganese-complex having the general formula:

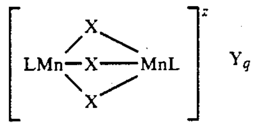

wherein Mn is manganese which can individually be in the III or IV oxidation state; each x represents a coordinating or bridging species selected from the group consisting of $H_2O$, $O_2^{2-}$, $O^{2-}$, $OH^-$, $HO_2^-$, $SH^-$, $S^{2-}$, >SO, $Cl^-$, $N^{3-}$, $SCN^-$, $RCOO^-$, $NH_2^-$ and $NR_3$, with R being H, alkyl or aryl, (optionally substituted); L is a ligand which is an organic molecule containing a number of nitrogen atoms which coordinates via all or some of its nitrogen atoms to the manganese centres; z denotes the charge of the complex and is an integer which can be positive or negative; Y is a monovalent or multivalent counter-ion, leading to charge neutrality, which is dependent upon the charge z of the complex; and $q = z/[\text{charge } Y]$, as a starch-removing additive in a chlorine bleach-free machine dishwashing composition comprising a peroxygen compound. Preferably, the machine dishwashing composition is a mildly alkaline product having a solution pH below 12, e.g. from 8–12, preferably from 9–11.

The solution pH as meant here is the pH as determined from a solution of 3 g/l of the composition in distilled water.

In a further aspect, the invention provides a non-chlorine bleach-containing machine dishwashing composition comprising from 0 to 80%, preferably from 5 to 60% by weight of a detergency and water-softening builder, from 0 to 80%, preferably 5 to 75% by weight of a buffering agent, from 1 to 40%, preferably from 2 to 20% by weight of peroxygen compound bleach, and optionally an enzyme, surfactant and fillers, characterized in that it further comprises a dinuclear manganese complex as defined above in an amount corresponding to an Mn-content of from 0.0001 to about 1.0% by weight, preferably from 0.0005 to 0.5% by weight.

Figure 1:
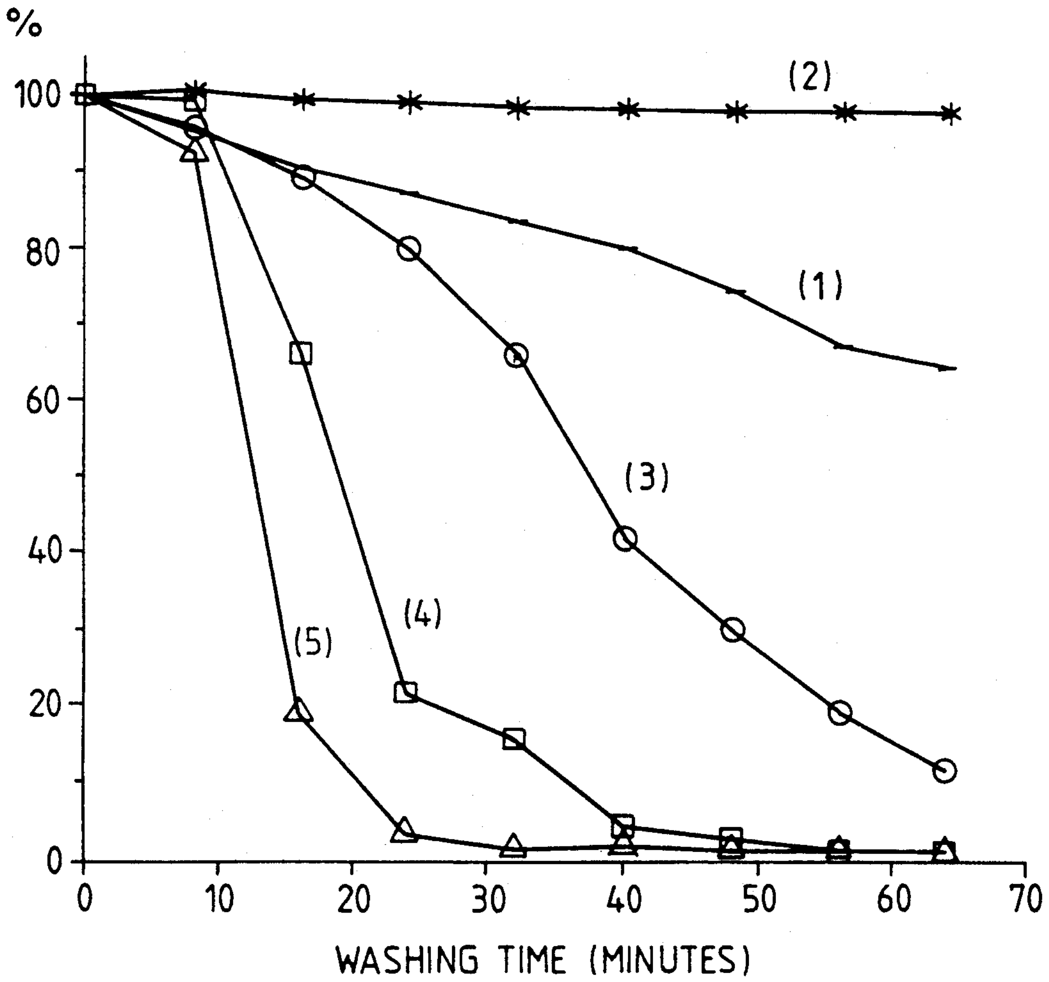
FIG. 1 is a graph representing the percentage residual pudding on glass versus washing time of the inventive compositions versus comparative compositions.

Preferred manganese-complexes are those wherein x is either $CH_3COO^-$ or $O^{2-}$ or mixtures thereof, most preferably wherein the manganese is in the IV oxidation state and x is $O^{2-}$. Preferred ligands are those which coordinate via three nitrogen atoms to one of the manganese centres, preferably being of a macrocyclic nature. Particularly preferred ligands are:

(1) 1,4,7-trimethyl-1,4,7-triazacyclonone, (Me-TACN), and (2) 1,2,4,7-tetrametyhyl-1,4,7-triazacyclononane, (Me-MeTACN).

The type of counter-ion Y for charge neutrality is not critical for the activity of the complex and can be selected from, for example, any of the following counter-ions: chloride; sulphate; nitrate; methylsulphate; surfactant anions, such as the long-chain alkylsulphates, alkylsulphonates, alkylbenzenesulphonates, tosylate; trifluoromethylsulphonate; perchlorate ($ClO_4^-$), $BPh_4^-$, and $PF_6^-$, though some counter-ions are more preferred than others for reasons of product property and safety.

Consequently, the preferred manganese complexes usable in the present invention are:

(I) $[(Me\text{-}TACN)Mn^{IV}(\mu\text{-}O)_3Mn^{IV}(Me\text{-}TACN)]^{2+}(PF_6^-)_2$ (II) $[(Me\text{-}MeTACN)Mn^{IV}(\mu\text{-}O)_3Mn^{IV}(Me\text{-}MeTACN)]^{2+}(PF_6^-)_2$ (III) $[(Me\text{-}TACN)Mn^{III}(\mu\text{-}O)(\mu\text{-}OAc)_2Mn^{III}(Me\text{-}TACN)]^{2+}(PF_6-)_2$ (IV) $[(Me\text{-}MeTACN)Mn^{III}(\mu\text{-}O)(\mu\text{-}OAc)_2Mn^{III}(Me\text{-}MeTACN)]^{2+}(PF_6-)_2$ which are hereinafter also abbreviated as:

(I) $[Mn^{IV}_2(\mu\text{-}O)_3(Me\text{-}TACN)_2](PF_6)_2$ (II) $[Mn^{IV}_2(\mu\text{-}O)_3(Me\text{-}MeTACN)_2](PF_6)_2$ (III) $[Mn^{III}_2(\mu\text{-}O)(\mu\text{-}OAc)_2(Me\text{-}TACN)_2](PF_6)_2$ (IV) $[Mn^{III}_2(\mu\text{-}O)(\mu\text{-}OAc)_2(Me\text{-}MeTACN)_2](PF_6)_2$ The structure of I is given below:

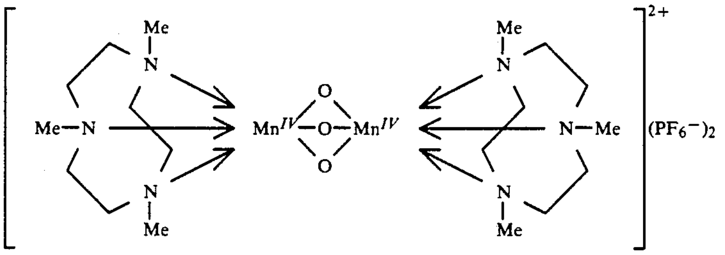

abbreviated as $[Mn^{IV}_2(\mu\text{-}O)_3(Me\text{-}TACN)_2](PF_6)_2$.

The structure of II is given below:

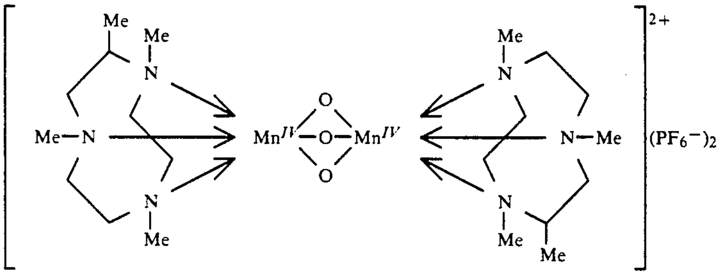

abbreviated as $[Mn^{IV}_2(\mu\text{-}O)_3(Me\text{-}MeTACN)_2](PF_6)_2$.

It is of note that the manganese complexes used in the present invention are reported in our co-pending U.S. application Ser. No. 703,554 and Ser. No. 703,555 as unusually effective bleach and oxidation catalysts. In the further description of the invention they will also be simply referred to as the "catalyst".

The discovery that these complexes are effective additives for starch removal in mechanical dishwashing compositions, even in the absence of amylolytic enzymes, is not known and must be surprising. It is furthermore surprisinq that, whereas amylolytic enzymes are not normally compatible with strong oxidizing and bleaching agents, the present bleach system comprising a peroxide compound and the manganese complex bleach catalyst does not seem to attack amylolytic enzymes, so that both systems can be used together to provide a still further improvement of starch removal.

THE PEROXYGEN COMPOUND

The peroxygen compound bleaches which can be utilized in the present invention include hydrogen peroxide, hydrogen peroxide-liberating compounds, hydrogen peroxide-generating compounds, as well as the organic and inorganic peroxyacids and water-soluble salts thereof.

Hydrogen peroxide sources are well known in the art. They include the alkali metal peroxides, organic peroxide bleaching compounds such as urea peroxide, and inorganic persalt bleaching compounds, such as the alkali metal perborates, percarbonates, perphosphates and persulphates. Mixtures of two or more of such compounds may also be suitable. Particularly preferred are sodium percarbonate and sodium perborate and, especially, sodium perborate monohydrate. Sodium perborate monohydrate is preferred to tetrahydrate because of its excellent storage stability while also dissolving very quickly in aqueous solutions. Sodium percarbonate may be preferred for environmental reasons. These bleaching agents may be utilized alone or in conjunction with a peroxyacid bleach precursor, such as TAED or any other bleach precursors known in the art, so long as it does not affect the starch-removing properties of the catalyst.

The organic peroxyacids usable in this invention are those compounds known in the art having normally one or more peroxycarboxyl groups

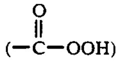

in their molecular structure, e.g. 1,12-diperoxydodecanedioic acid (DPDA) and phthaloylamido peroxycaproic acid (PAP). An inorganic peroxyacid salt usable herein is, for example, potassium monopersulphate.

THE BUILDER

The compositions of the invention will also normally contain a detergency and water-softening builder. Builder materials may be selected from 1) calcium sequestrant materials, 2) precipitating materials, 3) calcium ion-exchange materials and 4) mixtures thereof.

Examples of calcium sequestrant builder materials include alkali metal polyphosphates, such as sodium tripoly phosphate; nitrilotriacetic acid, dipicolinic acid, chelidamic acid and their water-soluble salts; the alkali metal salts of ether polycarboxylates, such as carboxymethyloxy succinic acid, oxydisuccinic acid, mellitic acid; ethylene diamine tetraacetic acid; benzene polycarboxylic acids; citric acid; and polyacetal carboxylates as disclosed in U.S. Pat. Nos. 4,144,226 and 4,146,495.

Examples of precipitating builder materials include sodium orthophosphate, sodium carbonate and sodium carbonate/calcite.

Examples of calcium ion-exchange builder materials include the various types of water-insoluble crystalline or amorphous aluminosilicates, of which zeolites are the best-known representatives. Other useful materials are, for example, layered silicates, such as SKS®-6 ex Hoechst.

In particular, the compositions of the invention may contain any one of the organic or inorganic builder materials, such as sodium or potassium tripolyphosphate, sodium or potassium pyrophosphate, sodium or potassium orthophosphate, sodium carbonate or sodium carbonate/calcite mixtures, the sodium salt of nitrilotriacetic acid, sodium citrate, carboxymethyl malonate, carboxymethyloxy succinate and the water-insoluble crystalline or amorphous aluminosilicate builder materials, or mixtures thereof.

Preferred compositions are, however, essentially free of phosphates and will contain, for example, sodium citrate, sodium carbonate, sodium carbonate/calcite, aluminosilicates (zeolites) or mixtures thereof as preferred builder materials.

An optional but highly desirable additive ingredient with multi-functional characteristics, particularly in non-phosphate compositions, is from 1% to 10%, preferably about 5% by weight of a polymeric material having a molecular weight of from 1,000 to 2,000,000 and which can be a homo- or co-polymer of acrylic acid, maleic acid, or salt or anhydride thereof, vinyl pyrrolidone methyl- or ethyl-, vinyl ethers and other polymerizable vinyl monomers. Preferred examples of such polymeric materials are polyacrylic acid or polyacrylate; polymaleic acid/acrylic acid copolymer; 70:30 acrylic acid/hydroxyethyl maleate copolymer; 1:1 styrene/maleic acid copolymer; isobutylene/maleic acid and diisobutylene/maleic acid copolymers; methyl- and ethyl-vinylether/maleic acid copolymers; ethylene/maleic acid copolymer; polyvinyl pyrrolidone; and vinyl pyrrolidone/maleic acid copolymer. These polymers are believed to function as co-builders, although under certain conditions they may also function as main builders.

THE BUFFERING AGENT

Buffering agents are necessary to adjust and to maintain the alkalinity and pH at the desired level. These are, for example, the alkali metal carbonates, bicarbonates, borates, and silicates. Usually, sodium silicates having $Na_2O:SiO_2$ ratios of from about 2:1 to 1:4 are the buffering agents most suitably used in machine dishwashing compositions. A preferred buffering agent is sodium disilicate having $Na_2O:SiO_2$ ratio of about 1:1.8 to 1:2.5.

THE ENZYMES

Though not essential, the cleaning compositions of the invention may, as desired, contain an amylolytic enzyme, though conceivably a much smaller amount will now be sufficient.

Reduction of the level of once an essential ingredient to even the possibility of omitting such an expensive enzyme ingredient, thereby resulting in improved performance, is one of the major advantages of the present invention, not only in terms technical benefit but also in terms of economy.

The amylolytic enzymes for use in the present invention can be those derived from bacteria or fungi. Preferred amylolytic enzymes are those prepared and described in British Patent Specification No 1 296 839, cultivated from the strains of *Bacillus licheniformis* NCIB 8061, NCIB 8059, ATCC 6334, ATCC 6598, ATCC 11 945, ATCC 8480 and ATCC 9945 A. Examples of such amylolytic enzymes are amylolytic enzymes produced and distributed under the trade-name of Sp-95® or Termamyl® by Novo Industri A/S, Copenhagen, Denmark. These amylolytic enzymes are generally presented as granules and may have enzyme activities of from about 2 to 10 Maltose units/milligram. Enzyme granules containing only minor proportions, e.g. less than 30%, particularly not more than 10% by weight of chloride to substantially nil, are preferably used in the compositions of the invention.

The amylolytic activity can be determined by the method as described by P. Bernfeld in "Method of Enzymology", Volume I (1955), page 149.

The composition of the invention preferably also contains a proteolytic enzyme.

Examples of suitable proteolytic enzymes are the subtilisins which are obtained from particular strains of

*B. subtilis and B. licheniformis,* such as the commercially available subtilisins Maxatase®, supplied by Gist-Brocades N.V., Delft, Holland, and Alcalase®, supplied by Novo Industri A/S, Copenhagen Denmark.

Particularly suitable is a protease obtained from a strain of Bacillus having maximum activity throughout the pH range of 8–12, being commercially available from Novo Industri A/S under the registered trade names of Esperase® and Savinase®. The preparation of these and analogous enzymes is described in British Patent No. 1 243 784. Another suitable protease useful herein is a fairly recent commercial product sold by Novo Industry A/S under the trade name "Durazym®", as described in WO-A-89/06279. These enzymes are generally presented as granules, e.g. marumes, prills, T-granulates etc., and may have enzyme activities of from about 500 to 1700 glycine units/milligram. The proteolytic activity can be determined by the method as described by M. L. Anson in "Journal of General Physiology", Vol. 22 (1938), page 79 (one Anson Unit/g=733 Glycine Units/milligram).

Enzyme granules containing only minor proportions, e.g. less than 30%, particularly not more than 10% by weight of chloride to substantially nil, are preferably used in the compostion of the invention.

If used, these enzymes can each be present in a weight percentage amounts of from 0.2 to 5% by weight, such that, for amylolytic enzymes, the final composition will have amylolytic activity of from $10^2$ to $10^6$ Maltose units/kg, and, for proteolytic enzymes, the final composition will have proteolytic enzyme activity of from about $10^6$ to $10^9$ Glycine Units/kg.

A small amount of low- to non-foaming nonionic surfactant, which includes any alkoxylated nonionic surface-active agent wherein the alkoxy moiety is selected from the group consisting of ethylene oxide, propylene oxide and mixtures thereof, is preferably used to improve the detergency and to suppress excessive foaming due to some protein soil. However, an excessive proportion of nonionic surfactant should be avoided. Normally, an amount of 0.1 to 7% by weight, preferably from 0.5 to 5% by weight, is quite sufficient.

Examples of suitable nonionic surfactants for use in the invention are the low- to non-foaming ethoxylated straight-chain alcohols of the Plurafac® RA series, supplied by the Eurane Company; of the Lutensol® LF series, supplied by the BASF Company; of the Triton® DF series, supplied by the Rohm & Haas Company, and of the Synperonic® LF series, supplied by the ICI company.

The composition of the invention may further contain any of the following additional ingredients. Stabilizing and anti-scaling agents, crystal-growth inhibitors and threshold agents. Examples of suitable stabilizing and anti-scaling compounds are those belonging to the class of phosphonates sold under the trade name "Dequest®", such as ethylene diamine tetra-(methylene phosphonate), diethylene triamine penta-(methylene phosphonate) and ethylene hydroxy diphosphonate. Another suitable class of anti-scaling agents are the low molecular weight polyacrylates, polymaleates and mixtures thereof or the copolymers thereof, having molecular weights of up to about 6000. A further suitable class of anti-scaling agents are polypeptides.

Clays, such as hectorites and montmorillonites, may be included in the composition of the invention. These assist in reduction of spot formation on glassware, and may be present at from 0.5 to 10% by weight, preferably from 0.5 to 7% by weight. Particularly preferred is the addition of Laponite® clay at about 0.5 to 5% by weight, which is a synthetic hectorite. "Dequest" and "Laponite" are Trade Marks owned by, respectively, Monsanto and Laporte Industries.

Finally, the addition of a filler may be required to complete the composition, though in compacted powdered compositions it should preferably be avoided. A preferred filler is sodium sulphate.

The invention will now be further illustrated by the following Examples.

EXAMPLE I

The following machine dishwashing base powder composition was used in comparative model dishwashing experiments carried out in 2-liter glass vessels on pudding-soiled glass slides (8 glass slides (5×5 cm) soiled with about 50 mg pudding in each experiment).

| Composition A | Parts by weight |
|---|---|
| sodium citrate | 43.0 |
| CP5-polymer ex BASF | 5.0 |
| sodium disilicate | 34.0 |
| proteolytic enzyme | 1.7 |
| Laponite clay | 1.7 |
| nonionic surfactant | 1.7 |

WASH CONDITIONS

Dosage: 3 g/l. Dishwashing product.
Water hardness: 16° FH (Ca/Mg=4:1)
Temperature: 55° C.
Manganese complex: $Mn^{IV}_2(\mu\text{-}O)_3(Me\text{-}TACN)_2](PF_6)_2$ at $10^{-5}$ Mol/l.

The rate of pudding removal was examined, using the base powder compostion with or without bleach and/or amylolytic enzyme "Termamyl" ex Novo Industry A/S.

The pudding removal was determined by weighing the residual amount of pudding present on the glass slides after washing.

The results are depicted in the graphs of FIG. 1 wherein % residual pudding is set out against washing time in minutes.

Bibliography

| | |
|---|---|
| Curve 1 (—) | Composition A + 6.8% sodiumperborate monohydrate<br>4.3% TAED<br>1.7% Termamyl (amylase) |
| Curve 2 (•) | Composition A + 6.8% sodiumperborate monohydrate<br>4.3% TAED |
| Curve 3 (o) | Composition A + 1.7% Termamyl |
| Curve 4 (□) | Composition A + 6.8% sodiumperborate monohydrate<br>$10^{-5}$ Mol/l. Mn-complex. |
| Curve 5 (Δ) | Composition A + 6.8% sodiumperborate monohydrate<br>1.7% Termamyl<br>$10^{-5}$ Mol/l. Mn-complex |

The data of FIG. 1 clearly demonstrate the superior performance of the compositions according to the invention. (Compare curves (4) and (5) with curves (1), (2) and (3)).

EXAMPLE II

For testing pudding removal from metals, the comparative model dishwashing experiments of Example I were repeated, wherein the glass slides were replaced by stainless steel slides.

Figure 2:
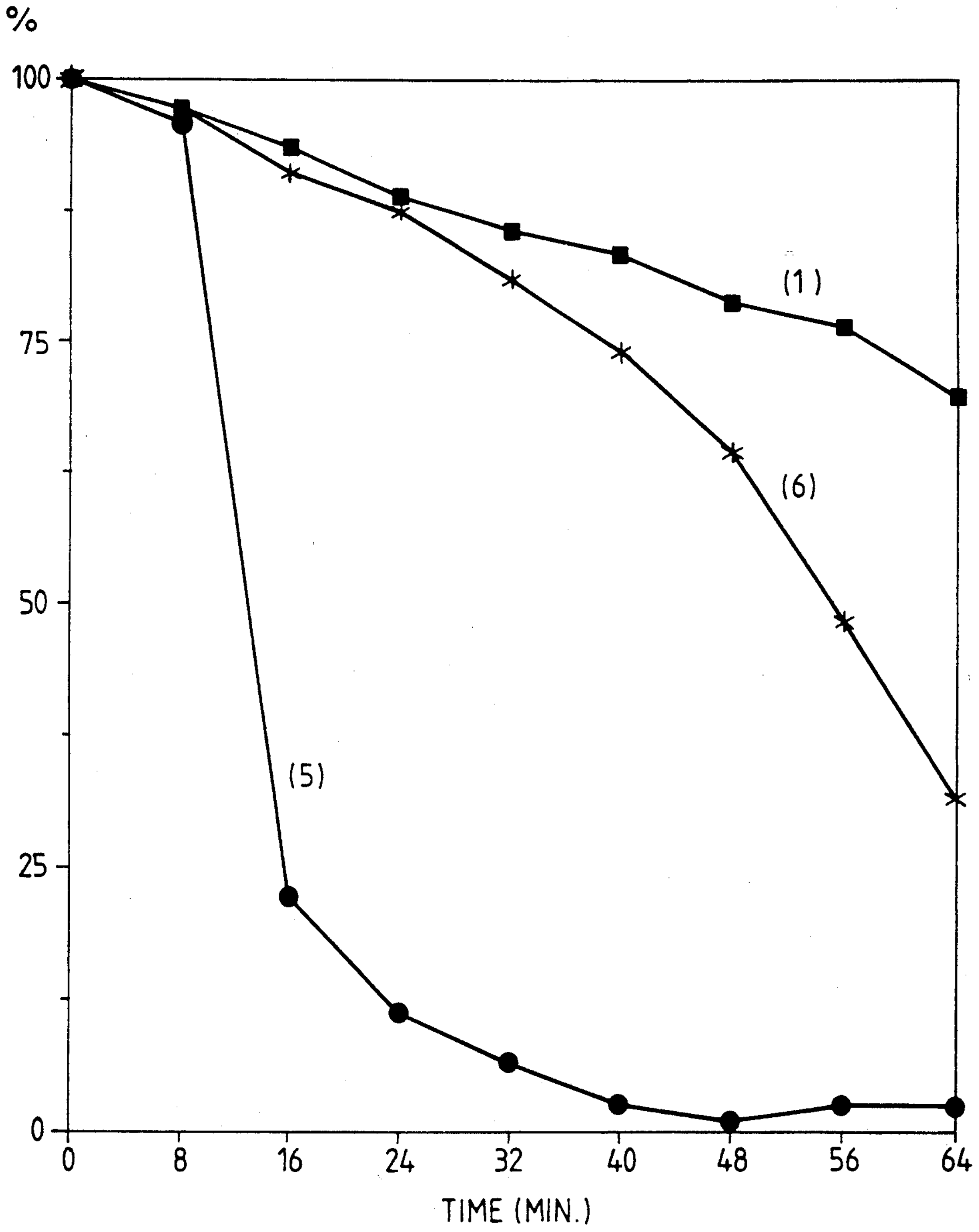
FIG. 2 is a graph illustrating the percent residual pudding on stainless steel versus washing time obtained when using the inventive compositions rather than prior art compositions.

The results are depicted in the graphs of FIG. 2, wherein % residual pudding is set out against washing time.

BIBLIOGRAPHY

| | |
|---|---|
| Curve 1 (■) | Composition A + 6.8% sodium perborate monohydrate<br>4.3% TAED<br>1.7% Termamyl (amylase) |
| Curve 6 (*) | Composition A + 6.8% sodiumperborate monohydrate<br>1.7% Termamyl |
| Curve 5 (●) | Composition A + 6.8% sodiumperborate monohydrate<br>1.7% Termamyl<br>$10^{-5}$ Mol/l Mn-complex. |

These data show that the composition of the invention (curve 5) is just as effective for the removal of pudding from metal surfaces and far superior to compositions of the art.

EXAMPLES III–IV

Machine evaluation was carried out in a Miele G 542 de Luxe dishwasher, using tap water of 16° FH with a saturated ion exchanger using the 55° C. universal programme. The base composition was Composition A of Example I and this was dosed at 3 g/l. The cleaning performance of each composition was evaluated, using a standard load comprising, amongst other articles, porcelain and stainless steel plates soiled with pudding.

The percentage of residual soil, which was used as criterion, was determined by subjective assessment of the surface area still covered with soil. The delta percentage residual soil was then found by subtracting the percentage found from washing without the Mn-comples by the percentage found from washing with the Mn-complex according to the invention.

EXAMPLE III (Mn-complex effect in the presence of amylase)

A comparison was made between Composition A+perborate+Termamyl+Mn-complex and Composition A+perborate+Termamyl—Mn-complex. The results, expressed as delta percentage residual soil after the wash, are shown below:

| | Δ% residual soil |
|---|---|
| Pudding on porcelain | 10% |
| Pudding on stainless steel | 21% |

EXAMPLE IV (Mn-complex effect in the absence of amylase)

A comparison was made between Composition A+perborate (+) Mn-complex and Composition A+perborate (−) Mn-complex. In this case, half the amount of the Mn-complex was used. The results are shown below:

| | Δ% residual soil |
|---|---|
| Pudding on porcelain | 27% |
| Pudding on stainless steel | 46% |

We claim:

1. A chlorine bleach-free machine dishwashing composition comprising:

a dinuclear manganese-complex having a formula

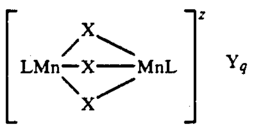

wherein Mn is manganese which can individually be in the III or IV oxidation state; each x represents a coordinating or bridging species selected from the group consisting of $H_2O$, $O_2^{2-}$, $O^{2-}$, $OH^-$, $HO_2^-$, $SH^-$, $S^{2-}$, >SO, $Cl^-$, $N^{3-}$, $SCN^-$, $RCOO^-$, $NH_2^-$ and $NR_3$, with R being H, alkyl or aryl substituted or unsubstituted; L is a ligand which is an organic molecule containing a number of nitrogen atoms which coordinates via all or some of its nitrogen atoms to the manganese centers; z denotes the charge of the complex and is an integer which can be positive or negative; Y is a mono-valent or multivalent counter-ion, leading to charge neutrality, which is dependent upon the charge z of the complex; and $q = z/[\text{charge } Y]$, used as a starch-removing additive, the dinuclear manganese-complex being present in an amount corresponding to a manganese content of from 0.0001 to about 1.0% by weight;

from 1 to 40% by weight of a peroxygen compound bleach;

from 0 to 80% by weight of a detergency and water softening builder;

from 0 to 80% by weight of a buffering agent; and form 0.2 to 5% by weight of an amylolytic enzyme such that the final composition has amylolytic enzyme activity of from $10^2$ to $10^6$ Maltose Units/kg.

2. A composition according to claim 1, wherein said dinuclear manganese complex is present in an amount corresponding to a manganese content of from 0.0005 to 0.5% by weight.

3. A composition according to claim 1, comprising from 5–60% by weight of builder, from 5 to 75% by weight of buffering agent, and from 2 to 40% by weight of peroxygen compound bleach.

4. A composition according to claim 1, wherein said composition has a solution PH below 12, as determined from a solution of 3 g/l of the composition in distilled water.

5. A composition according to claim 1, wherein x is $CH_3COO$; $O^{2-}$, or mixtures thereof.

6. A composition according to claim 1, wherein said dinuclear manganese complex is selected from compounds of the formulae:

$[(\text{Me-TACN})Mn^{IV}(\mu\text{-}O)_3Mn^{IV}(\text{Me-TACN})]^{2+}(PF_6^-)_2$ and $[(\text{Me-MeTACN})Mn^{IV}(\mu\text{-}O)_3Mn^{IV}(\text{Me-MeTACN})]^{2+}(PF_6^-)_2$ 7. A composition according to claim 1, wherein Mn is magnagnese in the IV oxidation state and x is $O^{2-}$.

8. A composition according to claim 1, further comprising a proteolytic enzyme in an amount such that the composition has proteolytic enzyme activity of from $10^6$ to $10^9$ Glycine Units/kg.

9. A composition according to claim 1, wherein L is a ligand which coordinates via three nitrogen atoms to one of the manganese centers.

10. A composition according to claim 9, wherein said ligand is selected from:

(1) 1,4,7-trimethyl-1,4,7-trizacyclononane (Me-TACN); and (2) 1,2,4,7-tetramethyl-1,4,7-triazacyclononane (Me-MeTACN).

11. A composition according to claim 10, wherein the manganese comples is $[(Me\text{-}TACN)MN^{IV}(\mu\text{-}O)_3Mn^{IV}(Me\text{-}TACN)]^{2+}(PF^{-}{}_6)_2$.

* * * * *